United States Patent [19]

Sikkenga et al.

[11] Patent Number: 5,012,024

[45] Date of Patent: Apr. 30, 1991

[54] PREPARATION OF A DIMETHYLNAPHTHALENE

[75] Inventors: David L. Sikkenga, Wheaton; Ian C. Zaenger, Glen Ellyn; Gregory S. Williams, Naperville, all of Ill.

[73] Assignee: Amoco Corporation, Chicago, Ill.

[21] Appl. No.: 316,309

[22] Filed: Feb. 27, 1989

Related U.S. Application Data

[63] Continuation-in-part of Ser. No. 210,999, Jun. 24, 1988, abandoned.

[51] Int. Cl.$^5$ .............................................. C07C 5/00
[52] U.S. Cl. .................................. 585/320; 585/430; 585/440; 585/481; 585/400
[58] Field of Search ............... 585/400, 440, 430, 320, 585/477, 480, 481

[56] References Cited

U.S. PATENT DOCUMENTS

| | | | |
|---|---|---|---|
| 3,775,496 | 11/1973 | Thompson | 585/320 |
| 3,781,375 | 12/1973 | Shima et al. | 585/400 |
| 3,803,253 | 4/1974 | Suld et al. | 585/481 |
| 3,957,896 | 5/1976 | Yokoyama et al. | 585/481 |

*Primary Examiner*—Chung K. Pak
*Attorney, Agent, or Firm*—James R. Henes; William H. Magidson; Ralph C. Medhurst

[57] ABSTRACT

A method for preparing one or more dimethylnaphthalenes from one or more dimethyltetralins, and optionally for preparing one or more other specific dimethylnaphthalenes by isomerization of the aforesaid dimethylnaphthal-dimethylnapthalene(s) is disclosed.

29 Claims, No Drawings

PREPARATION OF A DIMETHYLNAPHTHALENE

BACKGROUND OF THE INVENTION

1. Related Application

This application is a continuation-in-part of pending patent application Ser. No. 210,999, filed June 24, 1988, now abandoned.

2. Field of the Invention

This invention relates generally to a method for preparing one or more specific dimethylnaphthalene isomers by dehydrogenating one or more specific dimethyltetralin isomers.

3. Description of the Prior Art

Naphthalene dicarboxylic acids are monomers that are known to be useful for the preparation of a variety of polymers. For example, poly(ethylene 2,6-naphthalate) prepared from 2,6-naphthalene dicarboxylic acid and ethylene glycol has better heat resistance and mechanical properties than polyethylene terephthalate and is useful in the manufacture of films and fibers.

Dimethylnaphthalenes are desirable feedstocks for oxidation to the corresponding naphthalene dicarboxylic acids. A known conventional process for producing a naphthalene dicarboxylic acid comprises the oxidation of a dimethylnaphthalene with oxygen in the liquid phase in an acetic acid solvent at an elevated temperature and pressure and in the presence of a catalyst comprising cobalt, manganese and bromine components.

Typically dimethylnaphthalenes are found in refinery or coal-derived streams as mixtures of all of the ten possible dimethylnaphthalene isomers. However, separation of these isomers is very difficult and expensive. Consequently, methods for producing specific dimethylnaphthalenes or mixtures of two or three specific dimethylnaphthalenes in high purity and quality are highly desirable. One type of such method is a multistep synthesis involving (1) the formation of an alkenylbenzene by the reaction of o-, m- or p-xylene or ethylbenzene with butadiene, (2) the cyclization of the resulting alkenylbenzene to form one or more dimethyltetralins belonging to one or two of three groups of three isomeric dimethyltetralins—that is, either group A containing the 1,5-, 1,6-, 2,5- and 2,6-dimethyltetralins, group B containing the 1,7-, 1,8-, 2,7- and 2,8-dimethyltetralins, or group C containing the 1,3-, 1,4-, 2,3-, 5,7-, 5,8- and 6,7-dimethyltetralins—(3) the dehydrogenation of the dimethyltetralin(s) to form the corresponding dimethylnaphthalene(s), and (4) the isomerization of the resulting dimethylnaphthalene(s) to the desired specific dimethylnaphthalene.

For example, Thompson, U.S. Pat. Nos. 3,775,496; 3,775,497; 3,775,498; 3,775,500 disclose processes for the cyclization of specific alkenylbenzenes to one or more specific dimethyltetralins at 200°-450° C. in the presence of any suitable solid acidic cyclization catalyst such as acidic crystalline zeolites as well as silica-alumina, silica-magnesia and silica-alumina-zirconia and phosphoric acid, followed by the dehydrogenation of the resulting dimethyltetralin(s) in the vapor state to the corresponding dimethylnaphthalene(s) in a hydrogen atmosphere at 300°-500° C. and in the presence of a solid dehydrogenation catalyst such as noble metals on carriers and chromia-alumina, and thereafter isomerization of each of the aforesaid dimethylnaphthalene(s) to the desired isomer within the triad of dimethylnaphthalenes to which the isomer being isomerized belongs, at 275°-500° C. in the presence of a solid acidic isomerization catalyst of the same type as described in respect of the cyclization disclosed therein. In the alternative, both the cyclization and isomerization reactions can be performed in the liquid phase, in which case the cyclization is performed at 200°-275° C. with a solid phosphoric acid catalyst, at 70°-140° C. with an acidic ion exchange resin, an acidic crystalline zeolite, hydrofluoric or sulfuric acid as the catalyst or a siliceous cracking catalyst.

More specifically, Thompson, U.S. Pat. No. 3,775,496 discloses the cyclization of 5-(m-tolyl)-pent-2-ene to 1,6- and 1,8-dimethyltetralins, which are then dehydrogenated to 1,6- and 1,8-dimethylnaphthalenes, which in turn are isomerized to 2,6- and 2,7-dimethylnaphthalenes, respectively. Thompson, U.S. Pat. No. 3,775,497 discloses the cyclization of 5-phenyl-hex-2-ene to 1,4-dimethyltetralin which is then dehydrogenated to 1,4-dimethylnaphthalene, which is in turn isomerized to 2,3-dimethylnaphthalene. Thompson, U.S. Pat. No. 3,775,498 discloses the cyclization of 5-(o-tolyl)-pent-2-ene to 1,5-dimethyltetralin, which is then dehydrogenated to 1,5-dimethylnaphthalene, which is in turn isomerized to 2,6-dimethylnaphthalene. Thompson, U.S. Pat. No. 3,775,500 discloses the cyclization of 5-(p-tolyl)-pent-2-ene to 1,7-dimethyltetralin, which is then dehydrogenated to 1,7-dimethylnaphthalene, which in turn is isomerized to 2,7-dimethylnaphthalene.

Shimada et al., U.S. Pat. No. 3,780,119 disclose a method for the isomerization of dimethylnaphthalene by the use at a temperature above 260° C. of a mordenite catalyst in which a metal form of mordenite is in excess of 20 weight percent of the mordenite, with the metal being selected from the group consisting of lithium, sodium, potassium, magnesium, calcium, strontium, barium, zinc and aluminum.

Suld et al., U.S. Pat. No. 3,803,253 disclose a method for the hydroisomerization of a dimethylnaphthalene by the use of a combination of a hydrogenation catalyst and a calcium-containing zeolite catalyst, such as a calcium-exchanged synthetic faujasite, for example, a Y-type molecular sieve.

Shima et al., U.S. Pat. No. 3,806,552 disclose a method for the isomerization of dimethylnaphthalenes in the gas phase by the use of a mixed catalyst consisting of (a) 65-95 weight percent of a hydrogen form of mordenite in which above 80 weight percent of the metal cations are replaced with hydrogen ions, and (b) 5-35 weight percent of catalyst selected from the group consisting of bentonite and fuller's earth.

Hedge, U.S. Pat. No. 3,855,328 discloses a method for the isomerization of dimethylnaphthalenes by the use of a Type Y alumino silicate zeolite at 120°-300° C. in the liquid phase. The catalysts have aluminum-to-silicon atomic ratios of 0.1-1.0.

Ogasawara et al., U.S. Pat. No. 3,888,938 disclose a method for the isomerization of dimethylnaphthalenes in the liquid phase by the use of a mixed catalyst consisting of (a) 70-95 weight percent of a hydrogen form of mordenite in which above 80 weight percent of the metal cations are replaced with hydrogen ions, and (b) 5-30 weight percent of a promoter selected from the group consisting of bentonite and fuller's earth.

Hedge et al., U.S. Pat. No. 3,928,482 disclose the isomerization of either dimethyldecalins, dimethyltetralins or dimethylnaphthalenes in the presence of an alumino silicate zeolite containing polyvalent metal cations in exchange positions, such as a rare earth-exchanged Type Y zeolite.

Yokayama et al., U.S. Pat. No. 3,957,896 disclose the selective isomerization of dimethylnaphthalenes in the presence of any kind of natural or synthetic, solid acid catalyst, such as Y-type zeolite as well as silica-alumina, silica-magnesia, silica-zirconia, silica-aluminazirconia, fuller's earth, natural or synthetic mordenite, X-type zeolite, A-type zeolite and L-type zeolite. These catalysts may be substituted partly or wholly by hydrogen or metal. Furthermore, these catalysts can be unsupported or supported on carriers.

Onodera et al., U.S. Pat. No. 4,524,055 discloses a crystalline aluminosilicate zeolite that is useful in the isomerization of dimethylnaphthalenes and has a silica-to-alumina mole ratio of 10 to 100, specific x-ray lattice distances, and a specific cylohexane-to-n-hexane adsorption ratio of at least 0.7.

Maki et al., U.S. Pat. No. 4,556,751 disclose the isomerization of dimethylnaphthalenes in the presence of a crystalline aluminosilicate having a pentasil structure and a silica-to-alumina molar structure of 12 or higher. In addition, the aluminosilicate may contain some other metals as non-exchangeable metals.

A problem in all such prior art methods is the presence of other dimethylnaphthalene isomers and unconverted dimethyltetralin as impurities and by-products in the finally obtained, desired specific dimethylnaphthalene isomer. The presence of such impurities and by-products markedly reduces the utility and commercial value of the desired dimethylnaphthalene isomer, especially as a precursor for the formation of a naphthalene dicarboxylic acid for use as a monomer in the manufacture of a polymer. In addition, catalysts tend to deactivate relatively rapidly at the high temperatures employed in vapor phase processes. Therefore, it is highly desirable to employ relatively lower temperature liquid phase processes and to improve the completeness of each step in the aforesaid multistep synthesis and the selectivity of each step therein for the production of the desired product therefrom.

In this regard, it is known that in the presence of an acid catalyst, the dimethylnaphthalene isomers are isomerizable within each triad of dimethylnaphthalene isomers—that is, within the 1,5-, 1,6- and 2,6-dimethylnaphthalenes of triad A, within the 1,7-, 1,8-, and 2,7-dimethylnaphthalenes of triad B, and within the 1,3-, 1,4- and 2,3-dimethylnaphthalenes of triad C. It is also known that the interconversion of a dimethylnaphthalene isomer within one of the aforesaid triads to a dimethylnaphthalene isomer within another of the aforesaid triads occurs to a relatively lesser extent. However, it is highly desired to improve the selectivity and completeness of the aforesaid dehydrogenation and isomerization steps in the aforesaid multistep synthesis for the formation of the specific dimethylnaphthalene isomer(s) desired.

OBJECTS OF THE INVENTION

It is therefore a general object of the present invention to provide an improved method for manufacturing with an improved yield and selectivity a specific dimethylnaphthalene isomer or set of dimethylnaphthalene isomers which meets the aforementioned requirements for selectivity and completeness and catalyst activity.

It is a related object of the present invention to provide an improved method for manufacturing with an improved yield and selectivity a specific dimethylnaphthalene isomer or set of dimethylnaphthalene isomers by the dehydrogenation of a specific dimethyltetralin isomer or a set of dimethyltetralin isomers, and optionally then isomerizing the resulting first dimethylnaphthalene(s) to one or more other dimethylnaphthalene isomers that belong to the same triad or triads as do the first dimethylnaphthalene isomer(s).

Other objects and advantages of the method of the present invention will become apparent upon reading the following detailed description and appended claims.

SUMMARY OF THE INVENTION

The objects are achieved by an improved method for preparing a dimethylnaphthalene comprising: contacting a first feedstock comprising at least one dimethyltetralin in liquid form with a solid dehydrogenation catalyst in a reaction vessel at a temperature in the range of from about 200° C. to about 300° C. at a pressure that is sufficiently high to maintain the first feedstock substantially in the liquid phase, to thereby effect conversion of the aforesaid dimethyltetralin in an equilibrium dehydrogenation reaction to form hydrogen and a first liquid product comprising a dimethylnaphthalene formed from each aforesaid dimethyltetralin, and removing a substantial portion of the hydrogen being formed in the dehydrogenation reaction from the reaction vessel to thereby shift the aforesaid equilibrium toward the formation of the dimethylnaphthalene product.

DETAILED DESCRIPTION OF THE PREFERRED EMBODIMENTS

Any dimethyltetralin or mixture of dimethyltetralins is suitable for use as a feedstock in the method of this invention. In the method of the present invention, the dehydrogenation step is followed preferably by an isomerization step in which the dimethylnaphthalene(s) produced in the dehydrogenation step is isomerized to the desired dimethylnaphthalene(s). Thus, if a particular dimethylnaphthalene or set of dimethylnaphthalenes is desired as the final product, then it is preferred to use a dimethyltetralin or set of dimethyltetralins that form by the dehydrogenation of the method of the present invention either (1) such dimethylnaphthalene(s) directly or (2) other dimethylnaphthalene(s) which belong to the same triad or triads of dimethylnaphthalene isomers to which the desired dimethylnaphthalene isomer(s) belong, and which can then be isomerized in the preferred method of this invention to the desired dimethylnaphthalene(s).

In addition or in the alternative, the specific dimethyltetralin or set of specific dimethyltetralins employed in the dehydrogenation step of the method of this invention can depend on the manner in which each dimethyltetralin employed is obtained. For example, Sikkenga and Lamb, copending U.S. patent application Ser. No. 211,000, filed June 24, 1988 (the entire disclosure of which is specifically incorporated herein by reference), discloses the formation of one or more dimethyltetralins by the cyclization of 5-(o-, m-, or p-tolyl)-pent-1- or -2-ene or 5-phenyl-hex-1- or -2-ene, and thereafter the dehydrogenation of the resulting dimethyltetralin(s) to form one or more corresponding dimethylnaphthalenes.

When 5-(o-tolyl)-pent-1- or -2-ene is the feedstock to the aforesaid cyclization step, 1,5-, 1,6-, 2,5-, or 2,6-dimethyltetralin or a mixture thereof comprises at least 80, preferably at least 85 weight percent of the dimethyltetralins produced therefrom, which resulting dimethytetralins are in turn the feedstock and are converted in the dehydrogenation step of the present invention to the corresponding 1,5-, 1,6- and 2,6-dimethylnaphthalenes, which are then the feedstock in the isomerization step of the preferred embodiment of the present invention and are converted therein to 2,6-dimethylnaphthalene.

When 5-(m-tolyl)-pent-1- or -2-ene is the feedstock to the aforesaid cyclization step, 1,5- 1,6- 1,7-, 1,8-2,5- 2,6-, 2,7- or 2,8-dimethyltetralin or a mixture thereof comprises at least 80, preferably at least 85 weight percent of the dimethyltetralins produced therefrom, which dimethyltetralins are in turn the feedstock and are converted in the dehydrogenation step of the present invention to the corresponding 1,5-, 1,6-, 1,7-, 1,8- 2,6- and 2,7-dimethylnaphthalenes, which are then the feedstock in the isomerization step of the present invention and are converted therein to 2,6- and 2,7-dimethylnaphthalenes.

When 5-(p-tolyl)-pent-1- or -2-ene is the feedstock to the aforesaid cyclization step, 1,7-, 1,8-, 2,7- or 2,8-dimethyltetralin or a mixture thereof comprises at least 80, preferably at least 85 weight percent of the dimethyltetralins produced therefrom, which dimethyltetralins are in turn the feedstock and are converted in the dehydrogenation step of the present invention to the corresponding 1,7-, 1,8- and 2,7-dimethylnaphthalenes which are then the feedstock and are converted in the isomerization step of the present invention to 2,7-dimethylnaphthalene.

When 5-phenyl-1- or -2-hexene is the feedstock to the aforesaid cyclization step, 1,3-, 1,4-, 2,3-, 5,7, 5,8-, or 6,7-dimethyltetralin or a mixture thereof comprises at least 80, preferably at least 85 weight percent of the dimethyltetralins produced therefrom, which dimethyltetralins are in turn the feedstock and are converted in the dehydrogentation step of the present invention to the corresponding, 1,3-, 1,4- and 2,3-dimethylnaphthalenes, which are then the feedstock in the isomerization step of the present invention and are converted to 2,3-dimethylnaphthalene therein.

In the method of the present invention, each of the aforesaid dehydrogenation reaction and optional isomerization reaction is performed in the liquid phase at an elevated temperature and at a sufficiently high pressure to ensure that the feedstock for the particular step is maintained substantially in the liquid phase. The dehydrogenation reaction is performed at a temperature in the range of from about 200° C., preferably from about 220° C. to about 300° C., preferably to about 270° C. and generally at a pressure in the range of from about 0.5, preferably from about 0.8, to about 5, preferably to about 1.3 atmospheres absolute. The isomerization reaction is performed at a temperature in the range of from about 200° C., preferably from about 240° C., to about 300° C., preferably to about 280° C., and generally at a pressure in the range of from about 0.5, preferably from about 0.8, to about 5, preferably to about 1.3 atmospheres absolute.

Each of the dehydrogenation and isomerization reactions can be performed with or without a solvent for the respective feedstock. Preferably a solvent is not employed in the aforesaid steps. If employed, a solvent in any of the aforesaid steps must be inert under the conditions employed and suitably comprises a paraffin such as a tetradecane, or an aromatic hydrocarbon such as anthracene, or mixtures thereof, which preferably boils above about 270° C.

Each of the dehydrogenation and isomerization steps of the method of the present invention can be performed either batchwise or continuously. The reaction apparatus to be used in each aforesaid step can be of any known type such as a fixed bed, moving bed, fluidized bed, liquid phase suspended bed or a solid-liquid mixture in a stirred tank. Generally, however, the use of a fixed bed is commercially preferred for continuous operation.

The improved conversion of the feedstock and selectivity for the production of the desired product or set of products for each of the dehydrogenation and isomerization steps of the method of this invention are the result of the temperature and pressure conditions employed and the high activity and selectivity of the catalysts employed in each aforesaid step, which in turn permits the use of less severe conditions—that is, lower temperatures and pressures—such that greater selectivity and reduced catalyst deactivation can be achieved.

The catalyst employed in the dehydrogenation step of the method of this invention is any solid dehydrogenation catalyst that is capable of effecting the dehydrogenation and exhibiting a reasonable lifetime under the conditions employed, including catalysts such as noble metals on carriers such as reforming catalysts. Preferably, palladium on an active carbon or alumina support containing from about 0.5, more preferably from about 1.0, to about 15, more preferably to about 10 weight percent of palladium, calculated as elemental palladium and based on the weight of the catalyst, is employed as the dehydrogenation catalyst.

If the dehydrogenation is performed on a batch basis, the catalyst is employed at a level in the range of from about 0.005, preferably from about 0.01, to about 1.0, preferably to about 0.2 weight percent of the noble metal component, calculated as the elemental noble metal and based on the weight of the dimethyltetralin feedstock, and the reaction time is from about 1, preferably from about 2, to about 20, preferably to about 10 hours. If the dehydrogenation is performed on a continuous basis, the space velocity is in the range of from about 0.1, preferably from about 10, to about 100, preferably to about 50 parts of the dimethyltetralin feedstock per part of the noble metal component (calculated as the elemental noble metal) of the catalyst by weight per hour.

The catalyst employed in the isomerization step of the method of this invention comprises either beta zeolite or an acidic ultrastable—that is, a thermally stabilized or dealuminated—Y-type crystalline aluminosilicate zeolite having a silica-to-alumina molar ratio of from about 4:1 preferably from about 5:1, to about 10:1, preferably to about 6:1, and having pore windows provided by twelve-membered rings containing oxygen, and a unit cell size of from about 24.2, preferably from about 24.3, to about 24.7, preferably to about 24.6 angstroms. A suitable such zeolite is marketed by Union Carbide under the name LZ-Y72 or LZ-Y20. Water is not detrimental to catalytic activity or selectivity in the isomerization process.

The isomerization catalyst preferably comprises beta zeolite. The composition, structure and preparation of beta zeolite are described in Wadlinger et al., U.S. Pat. No. 3,308,069, which in its entirety is specifically incorporated herein by reference. The structure of beta zeolite is also reported in J. Haggen, "Structure of Zeolite Beta Determined," in Chemical & Engineering News, p. 23 (June 20, 1988). Beta zeolite is also commercially available from P.Q. Corporation.

The aforesaid ultrastable Y-type zeolite which can also be employed in the catalyst for the isomerization step of the method of this invention is in the hydrogen form and contains from about 0.01, preferably from about 1, up to about 5, preferably up to about 3 weight percent of sodium, calculated as elemental sodium and based on the weight of the zeolite.

Preferably the isomerization catalyst comprises a hydrogenation component comprising a Group VIII metal, which more preferably is palladium, platinum or nickel.

The aforesaid zeolite of the isomerization catalyst can be employed either unsupported or supported on a porous refractory, inorganic oxide that is inert under the conditions employed, such as silica, alumina, silica-alumina, magnesia, bentonite or other such clays. If a support is employed, preferably the support comprises silica, alumina or silica-alumina. When a support is employed, the zeolite comprises from about 10, preferably from about 20, to about 90, preferably to about 80 weight percent based on the weight of the catalyst.

If the isomerization is performed on a batch basis, the catalyst is employed at a level in the range of from about 0.1, preferably from about 1.0, to about 5, preferably to about 3 weight percent of the zeolite component of the catalyst, based on the weight of the dimethylnaphthalene feedstock, and the reaction time is from about 0.5, preferably from about 2, to about 10, preferably to about 6 hours. If the isomerization is performed on a continuous basis, the space velocity is in the range of from about 0.1, preferably from about 0.5 to about 10, preferably to about 5 parts of dimethylnaphthalene feedstock per part of zeolite component of the catalyst by weight per hour.

The present invention will be more clearly understood from the following specific examples.

EXAMPLES 1-6

In each of Examples 1-6, the liquid feed and a 5 weight percent palladium-on-carbon catalyst were charged to a flask and nitrogen was continuously passed through the reaction mixture to remove oxygen. The temperature of the reaction mixture was raised to the reaction temperature, and periodically samples were removed from the flask and analyzed. Hydrogen generated by the reaction was permitted to vent from the flask during the reaction. The experimental conditions employed, the compositions of the feedstock employed and of the resulting products containing up to 13 carbon atoms, the percent conversion of the feedstock, and the percent selectivity of the formation of desired product from the total amount of feedstock converted in each of Examples 1-6 are presented in Table 1.

The results in Table 1 illustrate that even with the mild temperature and pressure conditions employed in Examples 1-6, the dehydrogenation of the method of this invention affords both excellent conversion and selectivity.

TABLE 1

|  | Feed | Example 1 | | Example 2 | |
|---|---|---|---|---|---|
| Conditions |  |  |  |  |  |
| Hours on stream |  | 2.0 | 4.8 | 6.0 | 8.3 |
| Catalyst cycle no. |  | 1 | 1 | 1 | 1 |
| Temperature (°C.) |  | 242 | 243 | 245 | 244 |
| Pressure (psig) |  | 1.0 | 1.0 | 1.0 | 1.0 |
| Feed/catalyst weight ratio |  | 10.0 | 10.0 | 50.0 | 50.0 |
| Compositions (wt %) |  |  |  |  |  |
| 1,4-DMT | 0.0 | 0.0 | 0.0 | 0.0 | 0.0 |
| 1,5-DMT | 92.0 | 2.2 | 0.0 | 4.2 | 1.9 |
| 1,6-DMT | 0.0 | 0.0 | 0.0 | 0.0 | 0.0 |
| 1,7-DMT | 0.0 | 0.0 | 0.0 | 0.0 | 0.0 |
| 1,8-DMT | 0.0 | 0.0 | 0.0 | 0.0 | 0.0 |
| other DMTs | 0.1 | 0.4 | 0.2 | 0.3 | 0.0 |
| m-xylene | 0.1 | 0.6 | 0.5 | 0.5 | 0.3 |
| non-cyclic | 4.9 | 4.5 | 3.9 | 4.3 | 4.3 |
| Products |  |  |  |  |  |
| 1,3-DMN | 0.0 | 0.0 | 0.0 | 0.0 | 0.0 |
| 1,4-DMN | 0.0 | 0.0 | 0.0 | 0.0 | 0.0 |
| 1,5-DMN | 0.9 | 89.8 | 93.2 | 88.4 | 92.5 |
| 1,6-DMN | 0.0 | 0.5 | 0.5 | 0.4 | 0.0 |
| 1,7-DMN | 0.0 | 0.0 | 0.0 | 0.0 | 0.0 |
| 1,8-DMN | 0.0 | 0.0 | 0.6 | 0.2 | 0.0 |
| 2,6 + 2,7-DMNs | 0.0 | 0.0 | 0.0 | 0.0 | 0.0 |
| Lights | 0.1 | 1.5 | 1.0 | 1.1 | 0.6 |
| Heavies | 0.1 | 0.0 | 0.0 | 0.0 | 0.0 |
| Other | 1.8 | 0.5 | 0.1 | 0.5 | 0.4 |
| Total | 100.1 | 100.0 | 100.0 | 100.0 | 100.0 |
| Total DMNs |  | 90.3 | 94.3 | 89.0 | 92.5 |
| % Conversion |  | 97.6 | 100.0 | 95.4 | 98.0 |
| % Selectivity |  | 99 | 100 | 100 | 101 |

|  | Feed | Ex. 3 | Feed | Ex. 4 |
|---|---|---|---|---|
| Conditions |  |  |  |  |
| Hours on stream |  | 8.5 |  | 3.0 |
| Catalyst cycle no. |  | 1 |  | 1 |
| Temperature (°C.) |  | 251 |  | 253 |
| Pressure (psig) |  | 0.0 |  | 0.0 |
| Feed/catalyst weight ratio |  | 100.0 |  | 49.9 |
| Compositions (wt %) |  |  |  |  |
| 1,4-DMT |  |  |  |  |
| 1,5-DMT | 93.9 | 1.1 | 0.5 |  |
| 1,6-DMT | 0.6 |  | 0.8 |  |
| 1,7-DMT |  |  | 89.4 | 0.4 |
| 1,8-DMT |  |  |  |  |
| other DMTs | 1.2 | 0.3 | 0.1 | 0.0 |
| m-xylene | 0.1 | 0.3 | 0.0 | 0.0 |
| non-cyclic | 2.8 | 1.7 | 7.5 | 6.7 |
| Products |  |  |  |  |
| 1,3-DMN |  | 0.0 | 0.0 | 0.0 |
| 1,4-DMN |  | 0.0 | 0.0 | 0.2 |
| 1,5-DMN | 0.7 | 94.3 | 0.0 | 0.5 |
| 1,6-DMN |  | 0.8 | 0.0 | 0.8 |
| 1,7-DMN |  | 0.1 | 1.5 | 90.5 |
| 1,8-DMN |  | 0.4 | 0.0 | 0.1 |
| 2,6 + 2,7-DMNs |  | 0.0 | 0.0 | 0.3 |
| Lights |  | 0.7 | 0.0 | 0.1 |
| Heavies |  | 0.0 | 0.0 | 0.0 |
| Other | 0.6 | 0.4 | 0.0 | 0.2 |
| Total | 100.0 | 100.0 | 99.9 | 99.9 |
| Total DMNs |  | 95.5 | 1.5 | 92.4 |
| % Conversion |  | 98.8 |  | 99.5 |
| % Selectivity |  | 101 |  | 100 |

|  | Feed | Ex. 5 | Feed | Ex. 6 |
|---|---|---|---|---|
| Conditions |  |  |  |  |
| Hours on stream |  | 3.0 |  | 6.3 |
| Catalyst cycle no. |  | 1 |  | 1 |
| Temperature (°C.) |  | 254 |  | 254 |
| Pressure (psig) |  | 0.0 |  | 1.0 |
| Feed/catalyst weight ratio |  | 100.0 |  | 10.0 |
| Compositions (wt %) |  |  |  |  |
| 1,4-DMT | 92.7 | 0.4 |  |  |
| 1,5-DMT |  |  | 1.2 | 0.0 |
| 1,6-DMT |  |  | 55.2 | 0.0 |
| 1,7-DMT |  |  |  |  |
| 1,8-DMT |  |  | 36.0 | 1.4 |
| other DMTs | 0.0 | 3.6 | 1.0 | 0.0 |
| m-xylene |  |  |  | 0.4 |
| non-cyclic | 5.3 | 5.0 | 3.7 | 2.2 |
| Products |  |  |  |  |
| 1,3-DMN | 0.2 | 0.6 |  | 0.0 |
| 1,4-DMN | 1.6 | 90.2 |  | 0.0 |

TABLE 1-continued

|  |  |  |  |
|---|---|---|---|
| 1,5-DMN |  |  | 1.3 |
| 1,6-DMN |  | 0.9 | 58.2 |
| 1,7-DMN |  |  | 0.6 |
| 1,8-DMN |  |  | 35.6 |
| 2,6 + 2,7-DMNs |  |  | 0.2 |
| Lights | 0.4 |  | 0.3 |
| Heavies |  | 1.8 | 0.0 |
| Other |  | 0.3 |  | 0.0 |
| Total | 100.2 | 100.0 | 99.7 | 100.1 |
| Total DMNs |  | 90.8 |  | 95.8 |
| % Conversion |  | 99.5 |  | 98.5 |
| % Selectivity |  | 96.0 |  | 103.4 |

EXAMPLES 7–24

In each of Examples 7–24, the particular isomer of dimethylnaphthalene employed as the feed was mixed in liquid form with unsupported catalyst in a stirred reaction vessel with a continuous nitrogen purge to preclude oxygen from the system. The temperature of the reaction vessel was raised to the reaction temperature and samples were withdrawn at various times after commencement of the reaction and analyzed. The conditions employed, the compositions of the feedstock employed and of the resulting products containing up to 13 carbon atoms, the percent conversion of the feedstock, and the percent selectivity of the formation of desired product from the total amount of feedstock converted in each of Examples 7–24 are presented in Table 2.

The catalyst employed in Example 7 was a crystalline borosilicate molecular sieve (HAMS-1B from Amoco Chemical). The catalyst employed in Example 8 was Union Carbide's LZ-Y20 ultrastable Y-type sieve, containing 2 weight percent of copper, calculated as elemental copper. The catalyst employed in Example 9 was Union Carbide's LZ-Y62, a non-ultrastable, Y-type sieve in the ammonia exchanged form and having a unit cell size of 24.73Å. The catalyst employed in Examples 10 and 11 was commercially available Union Carbide's LZ-Y82, an ultra-stablemolecular sieve having a unit cell size of 24.56Å and a sodium content of less than 0.2 weight percent. In Example 10, the sieve was in the ammonia form and had not been calcined. In Example 11, the sieve had been calcined to form the hydrogen form. The catalyst employed in Example 12 was a commercially available amorphous silica-alumina containing 13 weight percent of alumina. The catalyst employed in Example 13 was commercially available mordenite in the acid form. The catalyst employed in Examples 14, 15 and 17–22 was commercially available Union Carbide's LZ-Y72 in the hydrogen form as received from the manufacturer. The catalyst employed in Example 16 was commercially available Grace USY sieve containing 2.6 weight percent of sodium and has chemical and physical properties that are very similar to those of Union Carbide's LZ-Y72, and is also suitable for use as a catalyst in either the cyclization or isomerization step in the method of this invention. 1,5-dimethylnaphthalene was the feed in Examples 7–21. The feed was 1,7-dimethylnaphthalene in Example 22 and 1,4-dimethylnaphthalene in Examples 23 and 24. For the purposes of Table 2, the concentration of 2,7-DMN in the product is taken to be approximately equal to the concentration of 1,7-DMN and is subtracted from the sum of 2,6-DMN and 2,7-DMN (which are determined together) for the purpose of determining the concentration of 2,6-DMN alone. The effective maximum concentrations of a particular desired DMN in its triad is its equilibrium concentration in the triad, which generally is 40–45 weight percent.

TABLE 2

|  | Feed | Ex. 7 | Feed | Ex. 8 | Feed | Ex. 9 | Ex. 10 | Ex. 11 | Ex. 12 | Ex. 13 |
|---|---|---|---|---|---|---|---|---|---|---|
| Conditions |  |  |  |  |  |  |  |  |  |  |
| Temperature (°C.) |  | 249 |  | 243 |  | 248 | 249 | 240 | 233 | 248 |
| Pressure (psig) |  | 1 |  | 1 |  | 1 | 1 | 1 | 1 | 1 |
| Catalyst |  | Amsac-3400 |  | LZ-20 |  | LZ-Y62 | LZ-Y82[1] | LZ-Y82[2] | SiO$_2$/Al$_2$O$_3$ | Mordenite[4] |
| Feed/catalyst wt ratio |  | 10 |  | 10 |  | 10 | 9.9 | 9.8 | 10.1 | 9.8 |
| Hours on stream |  | 7.3 |  | 13 |  | 12 | 11.8 | 5.5 | 13 | 11.5 |
| Product Composition (wt %) |  |  |  |  |  |  |  |  |  |  |
| 1,2-DMN | 0.0 | 0.0 | 0.0 | 0.1 | 0.0 | 0.0 | 0.0 | 0.4 | 0.0 | 0.0 |
| 1,3-DMN | 0.0 | 0.0 | 0.0 | 0.0 | 0.0 | 0.0 | 0.0 | 0.0 | 0.0 | 0.0 |
| 1,4-DMN | 0.0 | 0.0 | 0.0 | 0.0 | 0.0 | 0.0 | 0.0 | 0.0 | 0.0 | 0.0 |
| 1,5-DMN | 93.4 | 69.3 | 82.6 | 8.7 | 82.6 | 82.3 | 75.6 | 4.1 | 21.9 | 41.2 |
| 1,6-DMN | 0.0 | 20.1 | 11.8 | 37.8 | 11.8 | 12.1 | 18.3 | 25.4 | 42.8 | 29.4 |
| 1,7-DMN | 0.0 | 0.0 | 1.2 | 1.5 | 1.2 | 1.3 | 1.2 | 3.6 | 1.2 | 0.7 |
| 2,3-DMN | 0.0 | 0.0 | 0.0 | 0.0 | 0.0 | 0.0 | 0.0 | 1.2 | 0.0 | 0.0 |
| 2,6- + 2,7-DMNs | 0.0 | 5.4 | 1.8 | 36.3 | 1.8 | 2.1 | 3.2 | 30.4 | 29.3 | 27.6 |
| Lights | 6.3 | 2.6 | 1.7 | 1.4 | 1.7 | 1.8 | 1.2 | 1.3 | 1.2 | 1.0 |
| Heavies | 0.0 | 1.9 | 0.2 | 5.8 | 0.2 | 0.1 | 0.1 | 16.2 | 1.2 | 0.0 |
| Naphthalene | 0.0 | 0.0 | 0.0 | 0.1 | 0.0 | 0.0 | 0.0 | 0.7 | 0.0 | 0.0 |
| Methylnaphthalenes | 0.0 | 0.2 | 0.6 | 6.5 | 0.6 | 0.3 | 0.2 | 12.7 | 2.0 | 0.1 |
| Other | 0.2 | 0.5 | 0.0 | 1.9 | 0.0 | 0.0 | 0.0 | 3.9 | 0.5 | 0.0 |
| Total | 99.9 | 100.0 | 99.9 | 100.1 | 99.6 | 100.1 | 99.8 | 100.1 | 100.1 | 100.0 |
| Total DMNs | 93.4 | 94.8 | 97.3 | 84.4 | 97.3 | 97.8 | 98.3 | 65.1 | 95.2 | 98.9 |
| 2,7-DMN % |  |  |  |  |  |  |  |  |  |  |
| 2,6-DMN % in the 1,5-, 1,6- and 2,6-DMN triad | 0.0 | 5.7 | 0.6 | 42.8 | 0.6 | 0.9 | 2.1 | 47.7 | 30.3 | 27.6 |
| 2,6-DMN selectivity |  | 100 |  | 71.7 |  |  |  | 40.5 | 93.1 | >100 |

|  | Ex. 14 | Ex. 15 | Ex. 16 | Ex. 17 | Ex. 18 | Ex. 19 | Ex. 20 | Ex. 21 |
|---|---|---|---|---|---|---|---|---|
| Conditions |  |  |  |  |  |  |  |  |
| Temperature (°C.) | 226 | 227 | 252 | 251 | 248 | 248 | 249 | 248 |
| Pressure (psig) | 1 | 1 | 1 | 1 | 1 | 1 | 1 | 1 |
| Catalyst | LZY-72 | LZY-72 | US-Y[5] | LZY-72 | LZY-72 | LZY-72 | LZY-72 | LZY-72 |
| Feed/catalyst wt ratio | 50.4 | 50.4 | 50.8 | 50.6 | 50.6 | 50.6 | 50.6 | 50.6 |
| Hours on stream | 19.5 | 23.3 | 11.5 | 3.0 | 4.8 | 6.8 | 8.5 | 10.5 |

TABLE 2-continued

| Product Composition (wt %) | | | | | | | | |
|---|---|---|---|---|---|---|---|---|
| 1,2-DMN | 0.0 | 0.0 | 0.0 | 0.0 | 0.0 | 0.0 | 0.0 | 0.0 |
| 1,3-DMN | 0.0 | 0.0 | 0.0 | 0.0 | 0.0 | 0.0 | 0.0 | 0.0 |
| 1,4-DMN | 0.0 | 0.0 | 0.0 | 0.0 | 0.0 | 0.0 | 0.0 | 0.0 |
| 1,5-DMN | 24.0 | 21.3 | 17.5 | 20.9 | 15.1 | 12.2 | 9.6 | 8.7 |
| 1,6-DMN | 39.9 | 40.3 | 41.5 | 41.6 | 41.6 | 41.6 | 40.0 | 39.7 |
| 1,7-DMN | 1.0 | 0.9 | 1.0 | 0.9 | 1.0 | 1.0 | 1.2 | 1.2 |
| 2,3-DMN | 0.0 | 0.0 | 0.0 | 0.0 | 0.0 | 0.0 | 0.0 | 0.0 |
| 2,6- + 2,7-DMNs | 31.8 | 34.2 | 35.9 | 32.9 | 37.6 | 40.0 | 43.0 | 43.3 |
| Lights | 1.9 | 0.9 | 1.2 | 1.6 | 1.6 | 1.2 | 1.0 | 1.1 |
| Heavies | 0.9 | 1.1 | 1.0 | 0.8 | 1.1 | 1.6 | 2.1 | 2.2 |
| Naphthalene | 0.0 | 0.0 | 0.0 | 0.0 | 0.0 | 0.0 | 0.0 | 0.0 |
| Methylnaphthalenes | 1.0 | 1.1 | 1.3 | 1.1 | 1.5 | 1.7 | 2.6 | 2.8 |
| Other | 0.4 | 0.2 | 0.5 | 0.3 | 0.5 | 0.7 | 0.5 | 0.9 |
| Total | 100.9 | 100.0 | 99.9 | 100.1 | 100.0 | 100.0 | 100.0 | 99.9 |
| Total DMNs | 96.7 | 96.7 | 95.9 | 96.3 | 95.2 | 94.8 | 93.9 | 93.0 |
| 2,7-DMN % | 1.1 | | 1.1 | | | | | 1.6 |
| 2,6-DMN % in the 1,5-, 1,6- and 2,6-DMN triad | 32.5 | 35.1 | 37.2 | 33.8 | 39.2 | 42.0 | 45.7 | 46.5 |
| 2,6-DMN selectivity | 99.5 | 99.9 | 97.3 | 98.4 | 95.6 | 94.6 | 92.3 | 90.5 |

| | Feed | Ex. 22 | Feed | Ex. 23 | Ex. 24 |
|---|---|---|---|---|---|
| Conditions | | | | | |
| Temperature (°C.) | | 251 | | 247 | 252 |
| Pressure (psig) | | 1 | | 1 | 1 |
| Catalyst | LZY-72 | LZY-72 | LZY-72 | LZY-72 | LZY-72 |
| Feed/catalyst wt ratio | | 50.0 | | 44.0 | 44.0 |
| Hours on stream | | 4.0 | | 2.0 | 6.5 |
| Product Composition (wt %) | | | | | |
| 1,2-DMN | 0.0 | 0.0 | 0.0 | 0.1 | 0.4 |
| 1,3-DMN | 0.0 | 0.0 | 0.6 | 50.8 | 51.0 |
| 1,4-DMN | 0.0 | 0.0 | 90.6 | 15.1 | 9.0 |
| 1,5-DMN | 0.5 | 0.2 | 0.0 | 0.0 | 0.0 |
| 1,6-DMN | 0.7 | 1.4 | 0.0 | 0.0 | 0.0 |
| 1,7-DMN | 90.4 | 40.5 | 0.0 | 0.0 | 0.1 |
| 2,3-DMN | 0.0 | 0.0 | 0.0 | 22.1 | 23.3 |
| 2,6-DMN | 0.0 | 1.3 | 0.0 | 0.0 | 0.3 |
| 2,7-DMN | 0.3 | 44.7 | 0.0 | 0.0 | 0.1 |
| Lights | 6.6 | 6.3 | 5.2 | 4.3 | 3.6 |
| Heavies | 0.0 | 0.7 | 0.0 | 1.8 | 3.8 |
| Naphthalene | | | 0.0 | 2.0 | 3.3 |
| Methylnaphthalenes | 0.2 | 1.7 | 3.6 | 3.9 | 4.8 |
| Other | 1.3 | 2.8 | 0.0 | 0.0 | 0.3 |
| Total | 100.0 | 99.6 | 100.0 | 100.1 | 100.0 |
| Total DMNs | 92.0 | 88.4 | 91.1 | 88.1 | 84.2 |
| % desired DMN[1] in its triad | 0.3 | 52.2 | 0.6 | 25.1 | 28.0 |
| Selectivity | | 89.0 | | 87.5 | 74.8 |

Footnotes
[1]not calcined
[2]calcined
[3]13% $Al_2O_3$
[4]in H form
[5]ultrastable sieve containing 2.6% Na
[1]2,7-DMN in Example 22 and 2,3-DMN in Examples 23-24.

EXAMPLE 25

7.5 kilograms of distilled water, 7.5 kilograms of an aqueous solution containing 40 weight percent of tetraethylamine hydroxide, 50 grams of sodium hydroxide and 300 grams of sodium aluminate were stirred and dissolved in a 25-gallon stainless steel tank. The resulting solution and 12.2 kilograms of a silica sol containing 40 weight percent of silica were mixed and stirred in a 10-gallon autoclave at 150° C. for 72 hours. The resulting mixture was filtered, and the separated solids were washed three times with distilled water, dried at 120° C. and then calcined at 538° C. for 4 hours.

The resulting dried powder contained 0.37 weight percent of sodium, calculated as elemental sodium, and x-ray diffraction analysis indicated that the powder had the x-ray diffraction pattern of beta zeolite. The following is the x-ray diffraction pattern of the powder product, showing only the lines that are common to all 4 sources of beta zeolite in U.S. Pat. No. 3,308,069.

| Line d(A) | Relative Intensity |
|---|---|
| 4.18 | 16.2 |
| 3.99 | 100.0 |
| 3.54 | 6.1 |
| 3.35 | 12.6 |
| 3.11 | 3.0 |
| 3.05 | 14.6 |
| 2.94 | 5.3 |
| 2.69 | 4.1 |
| 2.54 | 1.5 |
| 2.08 | 11.5 |

The powder was employed as the catalyst without being ion-exchanged. Some powder was ion-exchanged using the ion-exchange procedure of Example 27 to reduce the sodium content, and after being ion-exchanged, the powder's alumina content, silica-to-alumina mole ratio and silicon-to aluminum atom ratio were measured as 1.14 weight percent, 68:1 and 34:1, respectively.

EXAMPLE 26

8 kilograms of distilled water, 8 kilograms of an aqueous solution containing 40 weight percent of tetraethylamine hydroxide, 3.81 kilograms of an aqueous solution containing 20 weight percent of tetraethylamine hydroxide, 0.6 kilogram of sodium aluminate, and 12.2 kilograms of a silica sol containing 40 weight percent of silica were mixed and stirred in a 10-gallon autoclave at 150° C. for 72 hours. The resulting mixture was filtered, and the separated solids were washed three times with distilled water, dried at 120° C. for about 16 hours and then calcined at 538° C. for 6 hours.

The resulting dried powder contained 0.17 weight percent of sodium, calculated as elemental sodium. X-ray diffraction analysis indicated that the powder had the x-ray diffraction pattern of beta zeolite. The following is the x-ray diffraction pattern of the powder product, showing only the lines that are common to all 4 sources of beta zeolite in U.S. Pat. No. 3,308,069.

| Line d(A) | Relative Intensity |
| --- | --- |
| 4.19 | 17.7 |
| 4.01 | 100.0 |
| 3.54 | Weak |
| 3.35 | 13.8 |
| 3.11 | Weak |
| 3.05 | 13.4 |
| 2.95 | 2.8 |
| 2.67 | Weak |
| 2.49 | 0.6 |
| 2.09 | 7.6 |

The powder was employed as the catalyst without being ion-exchanged. After being ion-exchanged using the procedure of Example 27 in order to reduce the sodium content, the powder's silica-to-alumina mole ratio and silicon-to-aluminum atom ratio were measured as 30:1 and 14.8:1, respectively.

EXAMPLE 27

2.3 kilograms of the un-ion-exchanged catalyst powder produced in Example 26, 4 kilograms of distilled water, and 12 kilograms of an aqueous solution containing 19 weight percent of ammonium nitrate were stirred in a 22-liter flask at 72° C. for 4 hours. The mixture was then cooled; the liquid was removed by decantation, and the resulting ion-exchanged catalyst was then washed with water. The catalyst was then dried at 120° C. and calcined at 538° C. for 3 hours. The ion-exchanged catalyst contained 0.01 weight percent of sodium (calculated as elemental sodium), 2.43 weight percent of aluminum (calculated as elemental aluminum), and a silica-to-alumina mole ratio and a silicon-to-aluminum atomic ratio of 30:1 and 14.8:1, respectively.

163 grams of this dry, ion-exchanged beta zeolite powder, 454 grams of an alumina sol containing 8.8 weight percent of solids, and 123 grams of distilled water were blended to obtain a smooth, uniform slurry. The slurry was maintained at 23° C. for 5 hours to permit liquid to evaporate from the slurry. The slurry was then dried at 120° C. for about 16 hours and calcined at 538° C. for 2 hours, to afford solids containing 80 weight percent of beta zeolite and 20 weight percent of alumina, which were then ground and sieved to form particles having a 20–40 mesh size.

EXAMPLES 28–46

In each of Examples 28–46, the particular feedstock employed was mixed in liquid form with a catalyst in a stirred reaction vessel with a continuous nitrogen purge to preclude oxygen from the system. The weight ratio of the feedstock-to-zeolite component of the catalyst was 49:1 in each case. The pressure of the contents of the reaction vessel was maintained at about 1 pound per square inch gauge. The temperature of the reaction vessel was raised to the reaction temperature and samples were withdrawn at various times after commencement of the reaction and analyzed. The conditions employed, the compositions of the feedstock employed and of the resulting products, the percent of the 1,5-, 1,6- and 2,6-DMN triad in each thereof, the percent of 2,6-DMN in each such 1,5-, 1,6- and 2,6-DMN triad, the percent decreases in each 1,5-, 1,6- and 2,6-DMN triad, the percent gain in each 1,7-, 1,8- and 2,7-DMN triad and the percent gain in total methylnaphthalene and trimethylnaphthalene content in each of Examples 28–46 are presented in Tables 3–7.

The catalyst employed in Examples 28–30 was commercially available Union Carbide's unsupported LZ-Y72 in the hydrogen form as received from the manufacturer. The catalyst employed in Examples 31–34 was an unsupported beta zeolite having a relatively high silicon-to-aluminum ratio and prepared by the procedure of Example 25. The catalyst employed in Examples 35–43 was an unsupported beta zeolite having a relatively low silicon-to-aluminum ratio and prepared by the procedure of Example 26. A single sample of this catalyst was used for four cycles in Examples 38–43. The catalyst employed in Examples 44–46 was also the beta zeolite having the relatively low silicon-to-aluminum ratio and prepared by the procedure of Example 26, but in this instance was ion-exchanged to reduce the sodium content and supported on an alumina matrix by the procedure of Example 27.

TABLE 3

| | Feed | Ex. 28 | Ex. 29 | Ex. 30 |
| --- | --- | --- | --- | --- |
| Conditions | | | | |
| Catalyst | | LZ-Y72 | LZ-Y72 | LZ-Y72 |
| Temperature (°C.) | | 250 | 250 | 250 |
| Hours on Stream | | 1 | 3 | 4.75 |
| Product | | | | |
| Composition (wt %) | | | | |
| 1,5-DMN | 91.03 | 38.70 | 18.30 | 12.84 |
| 1,6-DMN | 3.73 | 36.92 | 40.67 | 40.35 |
| 2,6-DMN | 0 | 18.42 | 32.40 | 36.18 |
| 1,7-DMN | 0.74 | 0.81 | 0.93 | 1.08 |
| 2,7-DMN | 0 | 0.73 | 1.37 | 1.81 |
| Methylnaphthalenes | 0.06 | 0.62 | 1.43 | 2.03 |
| Trimethylnaphthalenes | 0.44 | 0.53 | 1.33 | 2.02 |
| Other | 4.00 | 3.27 | 3.57 | 3.69 |
| Total | 100.00 | 100.00 | 100.00 | 100.00 |
| 1,5-, 1,6- and 2,6-DMN triad content | 94.76 | 94.04 | 91.37 | 89.37 |
| 2,6-DMN percent in 1,5-, 1,6- and 2,6-DMN triad | 0 | 19.59 | 35.46 | 40.49 |
| 1,5-, 1,6- and 2,6-DMN triad percent loss | 0 | 0.72 | 3.39 | 5.39 |
| 1,7-, 1,8- and 2,7-DMN triad percent gain | 0 | 0.80 | 1.56 | 2.15 |
| Methylnaphthalene and trimethylnaphthalene percent gain | 0 | 0.71 | 2.32 | 3.61 |

TABLE 4

| | Feed | Ex. 31 | Ex. 32 | Ex. 33 | Ex. 34 |
|---|---|---|---|---|---|
| Conditions | | | | | |
| Catalyst from Example | | 25 | 25 | 25 | 25 |
| Temperature (°C.) | | 250 | 250 | 250 | 250 |
| Hours on Stream | | 1 | 3 | 5 | 7 |
| Product Composition (wt %) | | | | | |
| 1,5-DMN | 91.03 | 54.00 | 28.93 | 18.94 | 14.09 |
| 1,6-DMN | 3.73 | 28.76 | 37.62 | 39.70 | 40.41 |
| 2,6-DMN | 0 | 12.91 | 28.76 | 35.96 | 39.55 |
| 1,7-DMN | 0.74 | 0.61 | 0.58 | 0.60 | 0.67 |
| 2,7-DMN | 0 | 0.67 | 1.09 | 1.13 | 1.28 |
| Methylnaphthalenes | 0 | 0.12 | 0.29 | 0.41 | 0.57 |
| Trimethylnaphthalenes | 0.44 | 0.10 | 0.19 | 0.34 | 0.46 |
| Other | 4.06 | 2.83 | 2.67 | 2.92 | 2.97 |
| Total | 100.00 | 100.00 | 100.00 | 100.00 | 100.00 |
| 1,5-, 1,6- and 2,6-DMN triad content | 94.76 | 95.67 | 95.18 | 94.60 | 94.05 |
| 2,6-DMN percent in 1,5-, 1,6- and 2,6-DMN triad | 0 | 13.49 | 30.08 | 38.01 | 42.05 |
| 1,5-, 1,6- and 2,6-DMN triad percent loss | 0 | −0.91 | −0.42 | 0.16 | 0.71 |
| 1,7-, 1,8- and 2,7-DMN triad percent gain | 0 | 0.54 | 0.93 | 0.99 | 1.21 |
| Methylnaphthalene and trimethylnaphthalene percent gain | 0 | −0.23 | 0.04 | 0.31 | 0.59 |

TABLE 5

| | Feed | Ex. 35 | Ex. 36 | Ex. 37 |
|---|---|---|---|---|
| Conditions | | | | |
| Catalyst from Example | | 26 | 26 | 26 |
| Temperature (°C.) | | 250 | 250 | 250 |
| Hours on Stream | | 1.25 | 3 | 5 |
| Product Composition (wt %) | | | | |
| 1,5-DMN | 91.03 | 21.94 | 10.79 | 8.20 |
| 1,6-DMN | 3.73 | 38.62 | 40.89 | 41.20 |
| 2,6-DMN | 0 | 35.59 | 43.28 | 44.94 |
| 1,7-DMN | 0.74 | 0.52 | 0.60 | 0.64 |
| 2,7-DMN | 0 | 0.30 | 0.53 | 0.47 |
| Methylnaphthalenes | 0 | 0.33 | 0.59 | 0.84 |
| Trimethylnaphthalenes | 0.44 | 0.16 | 0.46 | 0.78 |
| Other | 4.06 | 2.54 | 2.86 | 2.93 |
| Total | 100.00 | 100.00 | 100.00 | 100.00 |
| 1,5-, 1,6- and 2,6-DMN triad content | 94.76 | 96.15 | 94.96 | 94.34 |
| 2,6-DMN percent in 1,5-, 1,6- and 2,6-DMN triad | 0 | 37.02 | 45.58 | 47.63 |
| 1,5-,1,6- and 2,6-DMN triad percent loss | 0 | −1.39 | −0.20 | 0.42 |
| 1,7-,1,8- and 2,7-DMN triad percent gain | 0 | 0.08 | 0.39 | 0.37 |
| Methylnaphthalene and trimethylnaphthalene percent gain | 0 | 0.05 | 0.61 | 1.18 |

TABLE 6

| | Feed | Ex. 38 | Ex. 39 | Ex. 40 |
|---|---|---|---|---|
| Conditions | | | | |
| Catalyst from Example | | 26 | 26 | 26 |
| Temperature (°C.) | | 240 | 240 | 240 |
| Hours on Stream | | 3 | 3.9 | 3 |
| Catalyst Cycle | | 1st | 1st | 3rd |
| Product Composition (wt %) | | | | |
| 1,5-DMN | 88.14 | 9.63 | 7.99 | 26.62 |
| 1,6-DMN | 3.66 | 39.45 | 39.53 | 35.39 |
| 2,6-DMN | 0 | 41.50 | 42.34 | 29.83 |
| 1,7-DMN | 0.74 | 0.66 | 0.69 | 0.57 |
| 2,7-DMN | 0 | 1.26 | 1.50 | 1.02 |
| Methylnaphthalenes | 0.13 | 0.99 | 1.17 | 0.26 |
| Trimethylnaphthalenes | 0.54 | 0.53 | 0.70 | 0.17 |
| Other | 6.79 | 5.98 | 6.08 | 6.14 |
| Total | 100.00 | 100.00 | 100.00 | 100.00 |
| 1,5-, 1,6- and 2,6-DMN triad content | 91.80 | 90.58 | 89.86 | 91.84 |
| 2,6-DMN percent in 1,5-, 1,6- and 2,6-DMN triad | 0 | 45.82 | 47.12 | 32.48 |
| 1,5-, 1,6- and 2,6-DMN triad percent loss | 0 | 1.22 | 1.94 | −0.04 |
| 1,7-, 1,8- and 2,7-DMN triad percent gain | 0 | 1.18 | 1.45 | 0.85 |
| Methylnaphthalene and trimethylnaphthalene percent gain | 0 | 0.85 | 1.20 | −0.24 |

| | Feed | Ex. 41 | Ex. 42 | Ex. 43 |
|---|---|---|---|---|
| Conditions | | | | |
| Catalyst from Example | | 26 | 26 | 26 |
| Temperature (°C.) | | 240 | 265 | 265 |
| Hours on Stream | | 4.5 | 3 | 4.5 |
| Catalyst Cycle | | 3rd | 4th | 4th |
| Product Composition (wt %) | | | | |
| 1,5-DMN | 88.14 | 17.73 | 11.47 | 8.16 |
| 1,6-DMN | 3.66 | 38.10 | 39.23 | 39.73 |
| 2,6-DMN | 0 | 36.25 | 40.02 | 42.31 |
| 1,7-DMN | 0.74 | 0.59 | 0.66 | 0.72 |
| 2,7-DMN | 0 | 0.97 | 1.20 | 1.13 |
| Methylnaphthalenes | 0.13 | 0.33 | 0.48 | 0.70 |
| Trimethylnaphthalenes | 0.54 | 0.29 | 0.37 | 0.52 |
| Other | 6.79 | 5.74 | 6.57 | 6.73 |
| Total | 100.00 | 100.00 | 100.00 | 100.00 |
| 1,5-, 1,6- and 2,6-DMN triad content | 91.80 | 92.08 | 90.72 | 90.20 |
| 2,6-DMN percent in 1,5-, 1,6- and 2,6-DMN triad | 0 | 39.37 | 44.11 | 46.91 |
| 1,5-, 1,6- and 2,6-DMN triad percent loss | 0 | −0.28 | 1.08 | 1.60 |
| 1,7-, 1,8- and 2,7-DMN triad percent gain | 0 | 0.82 | 1.12 | 1.11 |
| Methylnaphthalene and trimethylnaphthalene percent gain | 0 | −0.05 | 0.18 | 0.55 |

TABLE 7

| | Feed | Ex. 44 | Ex. 45 | Ex. 46 |
|---|---|---|---|---|
| Conditions | | | | |
| Catalyst from Example | | 27 | 27 | 27 |
| Temperature (°C.) | | 250 | 250 | 250 |
| Hours on Stream | | 1 | 2 | 3 |
| Product Composition (wt %) | | | | |
| 1,5-DMN | 88.14 | 16.50 | 11.20 | 9.23 |
| 1,6-DMN | 3.66 | 38.10 | 39.30 | 39.70 |
| 2,6-DMN | 0 | 37.42 | 41.07 | 42.15 |
| 1,7-DMN | 0.74 | 0.53 | 0.55 | 0.58 |
| 2,7-DMN | 0 | 0.97 | 0.84 | 1.00 |
| Methylnaphthalenes | 0.13 | 0.52 | 0.69 | 0.83 |
| Trimethylnaphthalenes | 0.54 | 0.32 | 0.62 | 0.75 |
| Other | 6.79 | 5.64 | 5.73 | 5.76 |
| Total | 100.00 | 100.00 | 100.00 | 100.00 |
| 1,5-, 1,6- and 2,6-DMN triad content | 91.80 | 92.02 | 91.57 | 91.08 |
| 2,6-DMN percent in 1,5-, 1,6- and 2,6-DMN triad | 0 | 40.67 | 44.85 | 46.28 |
| 1,5-, 1,6- and 2,6-DMN triad percent loss | 0 | −0.22 | 0.23 | 0.72 |
| 1,7-, 1,8- and 2,7-DMN triad percent gain | 0 | 0.76 | 0.65 | 0.84 |
| Methylnaphthalene and trimethylnaphthalene | 0 | 0.17 | 0.64 | 0.91 |

TABLE 7-continued

| | Feed | Ex. 44 | Ex. 45 | Ex. 46 |
|---|---|---|---|---|
| percent gain | | | | |

Comparison of the results in Tables 3-7 illustrates clearly that (1) the use of a beta zeolite catalyst affords reduced losses of the 1,5-, 1,6- and 2,6-dimethylnaphthalene triad, reduced formation of methylnaphthalenes, trimethylnaphthalenes and the 1,7-, 1,8- and 2,7-dimethylnaphthalene triad relative to the use of the LZ-Y72 zeolite catalyst; and (2) the use of a beta zeolite catalyst either unsupported or supported on a base material and having a relatively lower silicon-to-aluminum ratio affords greater formation of 2,6-dimethylnaphthalene and reduced losses of the 1,5-, 1,6- and 2,6-dimethylnaphthalene triad relative to the use of a beta zeolite catalyst having a relatively higher silicon-to-aluminum ratio and permits the use of lower reaction temperatures or the use at a higher temperature of even a partially deactivated catalyst relative to the use of a LZ-Y72 zeolite catalyst.

From the above description, it is apparent that the objects of the present invention have been achieved. While only certain embodiments have been set forth, alternative embodiments and various modifications will be apparent from the above description to those skilled in the art. These alternatives are considered equivalents and are within the spirit and scope of the present invention.

Having described the invention, what is claimed is:

1. A method for preparing a dimethylnaphthalene, comprising: contacting a first feedstock comprising at least one dimethyltetralin in liquid form with a solid dehydrogenation catalyst in a reaction vessel at a temperature in the range of from about 200° C. to about 300° C. at a pressure that is sufficiently high to maintain the first feedstock substantially in the liquid phase, to thereby effect conversion of the aforesaid dimethyltetralin in an equilibrium dehydrogenation reaction to form hydrogen and a first liquid product comprising a dimethylnaphthalene formed from each aforesaid dimethyltetralin, and removing a substantial portion of the hydrogen being formed in the dehydrogenation reaction from the reaction vessel during the reaction to thereby shift the aforesaid equilibrium toward the formation of the dimethylnaphthalene product.

2. The method of claim 1 wherein either (a) 1,5-, 1,6-, 2,5-, or 2,6-dimethyltetralin or a mixture thereof comprises at least 80 weight percent of the dimethyltetralin content of the first feedstock, and 1,5-, 1,6- or 2,6-dimethylnaphthalene or a mixture thereof comprises at least 80 weight percent of the dimethylnaphthalene content of the first liquid product, (b) 1,5-, 1,6-, 1,7-, 1,8-, 2,5-, 2,6-, 2,7-, or 2,8-dimethyltetralin or a mixture thereof comprises at least 80 weight percent of the dimethyltetralin content of the first feedstock and 1,5-, 1,6-, 1,7-, 1,8-, 2,6-, or 2,7-dimethylnaphthalene or a mixture thereof comprises at least 80 weight percent of the dimethylnaphthalene content of the first liquid product, (c) 1,7-, 1,8-, 2,7- or 2,8-dimethyltetralin or a mixture thereof comprises at least 80 weight percent of the dimethyltetralin content of the first feedstock and 1,7-, 1,8- or 2,7-dimethylnaphthalene or a mixture thereof comprises at least 80 weight percent of the dimethylnaphthalene content of the first liquid product, or (d) 1,3-, 1,4-, 2,3-, 5,7-, 5,8- or 6,7-dimethyltetralin or a mixture thereof comprises at least 80 weight percent of the dimethyltetralin content of the first feedstock and 1,3-, 1,4- or 2,3-dimethylnaphthalene or a mixture thereof comprises at least 80 weight percent of the dimethylnaphthalene content of the first liquid product.

3. The method of claim 2 wherein 1,5-, 1,6-, 2,5-, or 2,6-dimethyltetralin or a mixture thereof comprises at least 80 weight percent of the dimethyltetralin content of the first feedstock and 1,5-, 1,6- or 2,6-dimethylnaphthalene or a mixture thereof comprises at least 80 weight percent of the dimethylnaphthalene content in the first liquid product.

4. The method of claim 2 wherein 1,5-, 1,6-, 1,7-, 1,8-, 2,5-, 2,6-, 2,7-, or 2,8-dimethyltetralin or a mixture thereof comprises at least 80 weight percent of the dimethyltetralin content of the first feedstock and 1,5-, 1,6-, 1,7-, 1,8-, 2,5-, 2,6-, or 2,7-dimethylnaphthalene or a mixture thereof comprises at least 80 weight percent of the dimethylnaphthalene content of the first liquid product.

5. The method of claim 2 wherein 1,7-, 1,8-, 2,7- or 2,8-dimethyltetralin or a mixture thereof comprises at least 80 weight percent of the dimethyltetralin content of the first feedstock, and 1,7-, 1,8- or 2,7-dimethylnaphthalene or a mixture thereof comprises at least 80 weight percent of the dimethylnaphthalene content of the first liquid product.

6. The method of claim 2 wherein 1,3-, 1,4-, 2,3-, 5,7-, 5,8- or 6,7-dimethyltetralin or a mixture thereof comprises at least 80 weight percent of the dimethyltetralin content of the first feedstock, and 1,3-, 1,4- or 2,3-dimethylnaphthalene or a mixture thereof comprises at least 80 weight percent of the dimethylnaphthalene content of the first liquid product.

7. The method of claim 2 wherein the dehydrogenation is performed at a temperature in the range of from about 220° C. to about 270° C.

8. The method of claim 2 wherein the dehydrogenation is performed at a pressure in the range of from about 0.5 to about 5 atmospheres absolute.

9. The method of claim 2 wherein the dehydrogenation catalyst comprises a noble metal component supported on a substantially inert support material, with the noble metal component employed at a level of from about 0.5 to about 15 weight percent, calculated as the elemental noble metal and based on the weight of the dehydrogenation catalyst.

10. The method of claim 9 wherein the noble metal component comprises palladium.

11. The method of claim 9 wherein the dehydrogenation is performed continuously with a space velocity in the range of from about 0.1 to about 100 parts of the feedstock per part of the noble metal component (calculated as the elemental noble metal) of the dehydrogenation catalyst by weight per hour.

12. The method of claim 9 wherein the dehydrogenation is performed on a batch basis with the dehydrogenation catalyst at a level in the range of from about 0.005 to about 1.0 percent of the noble metal component, calculated as the elemental noble metal, and based on the weight of the dimethyltetralin feedstock and the reaction time is from about 1 to about 20 hours.

13. The method of claim 2 wherein the second feedstock is dissolved in a solvent.

14. The method of claim 13 wherein the solvent is a paraffin or aromatic hydrocarbon which boils above about 270° C.

15. The method of claim 2 comprising the additional steps of: contacting the aforesaid first liquid product in liquid form with a solid isomerization catalyst comprising beta zeolite or an acidic ultrastable Y-crystalline zeolite having a silica-to-alumina molar ratio of from about 4 to about 10, and having pore windows provided by twelve-membered rings containing oxygen and a unit cell size of from about 24.2 to about 24.7, and at a temperature in the range of from about 200° C. to about 300° C. at a pressure that is sufficiently high to maintain the isomerization feedstock substantially in the liquid phase wherein (1) when at least 80 weight percent of the dimethylnaphthalene content of the first liquid product comprises at least one of 1,5-, 1,6-, and 2,6-dimethylnaphthalenes, at least 20 weight percent of the total of 1,5- and 1,6-dimethylnaphthalenes is isomerized to 2,6-dimethylnaphthalene, (2) when at least 80 weight percent of the dimethylnaphthalene content of the first liquid product comprises at least one of 1,5-, 1,6-, 1,7-, 1,8-, 2,6- and 2,7-dimethylnaphthalenes, at least 20 weight percent of the total of 1,5-, 1,6-, 1,7- and 1,8-dimethylnaphthalenes is isomerized to 2,6- and 2,7-dimethylnaphthalenes, (3) when at least 80 weight percent of the dimethylnaphthalene content of the first liquid product comprises at least 1,7-, 1,8- and 2,7-dimethylnaphthalene at least 20 weight percent of the total of 1,7- and 1,8-dimethylnaphthalenes is isomerized to 2,7-dimethylnaphthalene, and (4) when at least 80 weight percent of the dimethylnaphthalene content comprises at least one of 1,3-, 1,4- and 2,3-dimethylnaphthalenes, at least 20 weight percent of the total of 1,3- and 1,4-dimethylnaphthalenes is isomerized to 2,3-dimethylnaphthalene.

16. The method of claim 15 wherein at least 25 weight percent of the total of 1,5- and 1,6-dimethylnaphthalenes in the aforesaid first liquid product in (1) of claim 15 is isomerized to 2,6-dimethylnaphthalene.

17. The method of claim 15 wherein at least 25 weight percent of the total of 1,5-, 1,6-, 1,7- and 1,8-dimethylnaphthalenes in the aforesaid first liquid product in (2) of claim 15 is isomerized to 2,7-dimethylnaphthalene and 2,6-dimethylnaphthalene.

18. The method of claim 15 wherein at least 25 weight percent of the total of 1,7- and 1,8-dimethylnaphthalenes in the aforesaid first liquid product in (3) of claim 15 is isomerized to 2,7-dimethylnaphthalene.

19. The method of claim 15 wherein at least 25 weight percent of the total of 1,3- and 1,4-dimethylnaphthalenes in the aforesaid first liquid product in (4) of claim 15 is isomerized to 2,3-dimethylnaphthalene.

20. The method of claim 15 wherein the isomerization is performed at a temperature in the range of from about 240° C. to about 280° C.

21. The method of claim 15 wherein the isomerization is performed on a batch basis.

22. The method of claim 15 wherein the isomerization catalyst employed comprises beta zeolite.

23. The method of claim 22 wherein the isomerization catalyst comprises a hydrogenation component comprising a Group VIII metal.

24. The method of claim 23 wherein the Group VIII metal is palladium, platinum or nickel.

25. The method of claim 21 wherein the isomerization catalyst employed is free of a support material.

26. The method of claim 21 wherein the isomerization catalyst is supported on an inorganic support material.

27. The method of claim 26 wherein the support material comprises silica, alumina, silica-alumina, or bentonite, or magnesia, or a mixture thereof.

28. The method of claim 15 wherein the isomerization is performed at a pressure in the range of from about 0.3 to about 5 atmospheres absolute.

29. The method of claim 15 wherein the isomerization is performed on a continuous basis with a space velocity of, or on a batch basis with an effective space velocity of, from about 0.2 to about 20 parts of feedstock per part of the zeolite component of the isomerization catalyst by weight per hour.

* * * * *

UNITED STATES PATENT OFFICE
CERTIFICATE OF CORRECTION

Patent No. 5,012,024                    Dated  April 30, 1991

Inventor(s)  David L. Sikkenga, Ian C. Zaenger, Gregory S. Williams

It is certified that error appears in the above-identified patent and that said Letters Patent is hereby corrected as shown below:

| Col. | Line | |
|---|---|---|
| Abst. | 4-5 | "dimethyl-naphthal-dimethylnaphthalene" should read --dimethylnaphthalene-- |
| 3 | 17 | "cylohexane" should read --cyclohexane-- |
| 5 | 9 | "1,8-2,5-" should read --1,8- 2,5- -- |
| 10 | 5 | "ulta-stablemolecular" should read --ultra-stable molecular-- |
| 10 Table | 42-43 Ex. 8 | "10" (after LZ-20) should read --2% Cu-- |
| 12 | 68 | "to aluminum" should read --to-aluminum-- |

Signed and Sealed this

Twenty-ninth Day of September, 1992

Attest:

DOUGLAS B. COMER

Attesting Officer          Acting Commissioner of Patents and Trademarks